Figure 1:
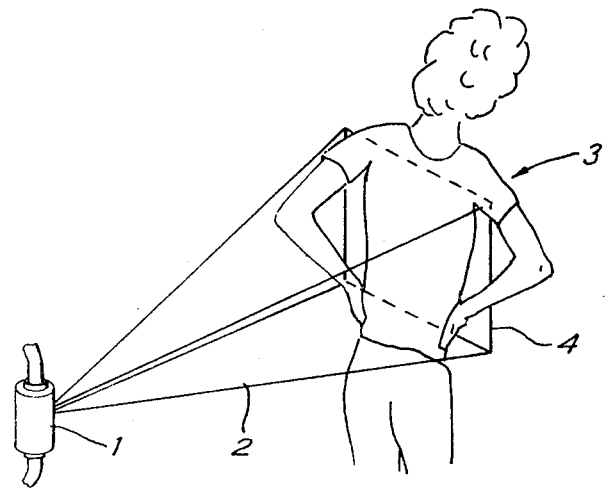

United States Patent [19]

Dalton et al.

[11] 4,365,161

[45] Dec. 21, 1982

[54] DETECTOR FOR RESPONDING TO A TWO-DIMENSIONAL PATTERN OF X-RADIATION

[75] Inventors: Brian L. Dalton, London; Robert J. Froggatt, Southall, both of England

[73] Assignee: E M I Limited, Hayes, England

[21] Appl. No.: 175,719

[22] Filed: Aug. 6, 1980

[30] Foreign Application Priority Data

Aug. 10, 1979 [GB] United Kingdom ............... 7927968

[51] Int. Cl.³ ..................... H05G 1/60; A61B 6/00; H01J 39/28
[52] U.S. Cl. ..................................... 378/99; 250/385
[58] Field of Search ................... 250/416 TV, 385

[56] References Cited

U.S. PATENT DOCUMENTS 3,101,407 8/1963 Shipman ..................... 250/71.5
3,418,474 12/1968 Spergel et al. ................ 250/385
4,253,025 2/1981 Fergus ......................... 250/385

FOREIGN PATENT DOCUMENTS 2250120 5/1975 France ........................ 250/385

Primary Examiner—Alfred E. Smith
Assistant Examiner—T. N. Grigsby
Attorney, Agent, or Firm—Fleit & Jacobson

[57] ABSTRACT

The invention relates to a flat plate X-ray detector. In one example a back plate of a flat xenon detector has coaxial cables in a conducting solid matrix connected to the power supply. Each cable center conductor is a small capacitor which charges in response to ion collection. The signals are derived via a commutator.

In another embodiment the back plate is an anisotropic plate discharged in a spiral pattern similar to a gramophone record groove.

7 Claims, 6 Drawing Figures

DETECTOR FOR RESPONDING TO A TWO-DIMENSIONAL PATTERN OF X-RADIATION

This invention relates to radiography, and it relates more particularly to the form of radiography conventionally used for chest X-rays, in which a source of a pyramidal or conical shaped beam of radiation and a flat, plate-like X-ray detector are disposed on opposite sides of a patient. The source is energised for a short time to pass X-rays through the patient and the detector responds to the radiation transmitted through the patient to develop a two-dimensional image of the emergent radiation pattern.

Conventionally, the X-ray detector is constituted by an X-ray sensitive film and the image is produced by processing the film in known manner. There are, however, many advantages to be gained from utilising a detector which responds to the two-dimensional pattern of radiation emergent from the patient to generate electrical signals indicative of the pattern. One advantage of utilising such a detector is that the electrical signals can be subjected to various processing techniques that can improve the usefulness of the image with regard to clinical diagnosis. For example, the signals may be filtered, spatially and/or in frequency. Moreover, the signals could be subjected to windowing control, by means of which the extent and/or the mean level of the dynamic range of the signals can be adjusted.

These advantages have been recognised for some time, but a difficulty has arisen in constructing a suitable two-dimensional detector which is capable of providing discrete output signals for many locations, distributed over the two dimensions, as dictated by the resolution required in the image.

One approach, disclosed in U.S. Pat. No. 3,101,407 has been to utilise a source of a flat fan of radiation and a one-dimensional array of detectors, and to scan both the source and the detector array along the patient so as to gradually build up a two-dimensional image of part of the patient's body. This approach, however, is subject to a number of disadvantages.

Firstly, it is not compatible with existing film-based systems, as would be desirable to enable existing systems to be updated to take advantage of electronic detectors and associated processing. Secondly, it calls for a scanning movement to be imparted synchronously and concomitantly to the source and the detector array. It is undesirable to have to provide such scanning movement. Thirdly, the flat fan-shaped distribution of X-rays is produced by collimating the conical or pyramidal shaped beam that is produced by the X-ray source (e.g. a rotating anode X-ray tube) and this is wasteful in terms of source efficiency and operation.

It is the object of this invention to provide a two-dimensional X-ray detector arrangement that generates electrical signals in response to the pattern of radiation emergent from a patient and in which the difficulty referred to above is reduced or eliminated without introducing the disadvantages associated with the approach of the aforementioned United States Patent.

According to the invention there is provided a detector for responding to a two-dimensional pattern of X-radiation emergent from an object under examination to generate discrete electrical signals indicative of the amounts of radiation received at each of many locations distributed over the pattern, said detector comprising a substantially flat chamber, containing a noble gas, with an X-ray pervious input window disposed to receive said pattern of radiation and a back-plate for said chamber disposed opposite said window and containing a respective electrical contact member for each of said locations, the contact members being exposed to said gas and mutually insulated so as to create an array of capacitive probes each capable, when suitable operating potentials are applied to the chamber, of storing charge indicative of the amount of radiation at the appropriate location of said pattern.

Figure 2:
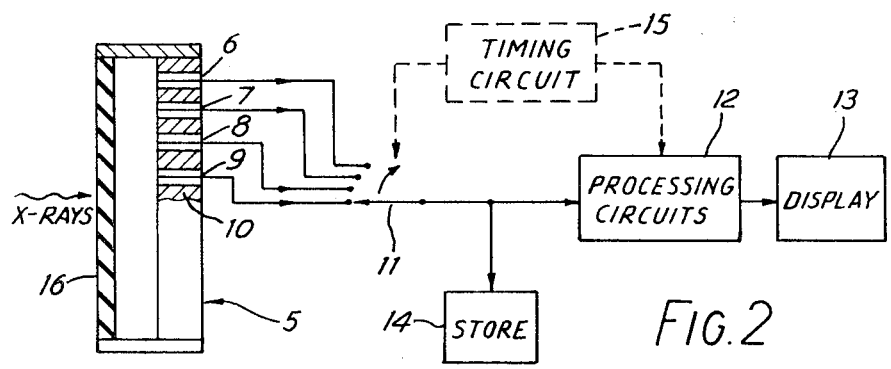

In order that the invention may be clearly understood and readily carried into effect, some embodiments thereof will now be described, by way of example only, with reference to the accompanying drawings of which:

FIG. 1 shows, in perspective view, the basic elements of a radiographic system employing one embodiment of the present invention, FIG. 2 shows, partly in cross section and partly in block diagrammatic form, a detector arrangement in accordance with one example of this invention and some associated electrical circuits, FIGS. 3a and 3b show, in plan and elevation respectively, a detector arrangement in accordance with another example of this invention.

Figure 4:
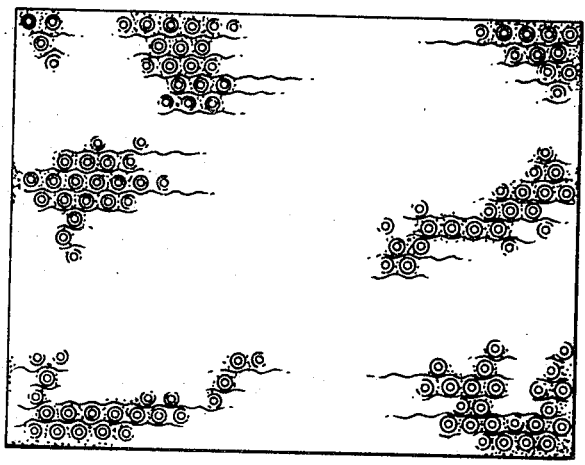
Figure 5:
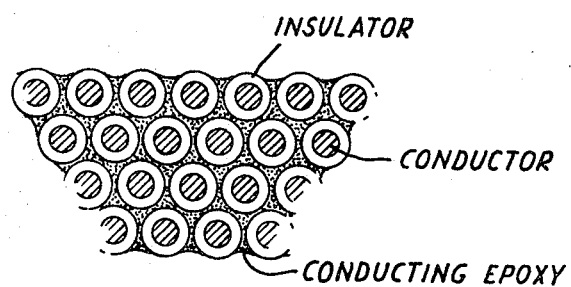

FIG. 4 is a copy of a photomicrograph showing a detector plate for use in connection with the invention, and FIG. 5 shows a fragment of another example of a detector plate.

Referring now to FIG. 1, a source 1 of a conical or pyramidal beam 2 of X-radiation is supported and disposed so as to irradiate part of the body of a patient 3. A two-dimensional detector arrangement 4 is disposed at the opposite side of the patient to the source so as to receive the pattern of X-radiation emergent from the body part. In this example, the detector arrangement 4 comprises a sealed chamber containing a noble gas, preferably Xenon under pressure, that ionises in response to the X-radiation emergent from the body, the extent to which ionisation occurs at each part of the chamber being determined by the amount of X-radiation impinging upon that part of the chamber. There is thus an ionisation pattern in the xenon chamber which corresponds to the pattern of X-radiation emergent from the body part. The application of suitable potentials to the chamber permits the electrons and ions generated in the chamber to be collected by means of suitable electrodes, and this permits the generation of electrical signals indicative of the radiation pattern incident upon the chamber.

However, although it is possible to provide individual electrodes for the various locations of the chamber for which electrical signals are required, it is undesirable to have to connect each individual electrode to a respective processing circuit. It is preferable to serialise the signals from the various electrodes so that they can be applied sequentially, instead of simultaneously, to the various processing circuits (e.g. windowing circuits). This preference for serialisation of the output signals requires the charge pattern, resulting from the collection by the electrodes of the ionisation pattern, to be stored for long enough to permit the various electrodes to be scanned in sequence so as to liberate the charge therefrom.

In accordance with this example of the invention, and as shown schematically in FIG. 2, the back-plate 5 of the xenon chamber is constructed from a multiplicity of close-packed, parallel coaxial cables such as 6, 7, 8 and 9 immersed in a matrix 10 of an electrically conductive solid connected to the electrical supply which applies the ion-collecting potentials to the xenon chamber 4. Thus the central conductor of each coaxial cable forms a small capacitor on which the charge, pertaining to the location of the chamber at which that cable is disposed, can be stored. Since one end of the cable is inside the chamber, it will charge up in response to the collection of ions from the relevant location of the chamber and the other end can be interrogated, when the X-ray exposure is complete, by a serialiser, such as a mechanical commutator 11. Signals provided by the commutator 11 are processed in processing circuits 12 and then displayed at 13. It can be advantageous to record the unprocessed signals so that they are available for future use if required, and FIG. 2 shows a store 14, for example a magnetic core store, connected to achieve this.

It can, of course, be advantageous to utilise an electronic commutator instead of a mechanical device, and in those circumstances, the switching of the commutator 11 can be controlled from an electrical timing circuit 15 that also controls the processing circuit 12 and enables different functions to be applied to signals derived from different parts of the chamber should this be desired.

It will be appreciated that, although only four coaxial cables are shown in the drawing, in practice many hundreds or thousands of such cables may be called for. It will also be appreciated that the cables could be arranged in a square matrix layout or in any other convenient layout, such as a spiral or zig-zag.

The circuit and electrodes for applying the ion-collecting voltages to the xenon chamber are not shown as they are known of themselves and not material to this invention. It will be appreciated that the chamber is formed with an X-ray transmissive window 16 through which the pattern of X-rays travels to ionise the xenon.

Figure 3:
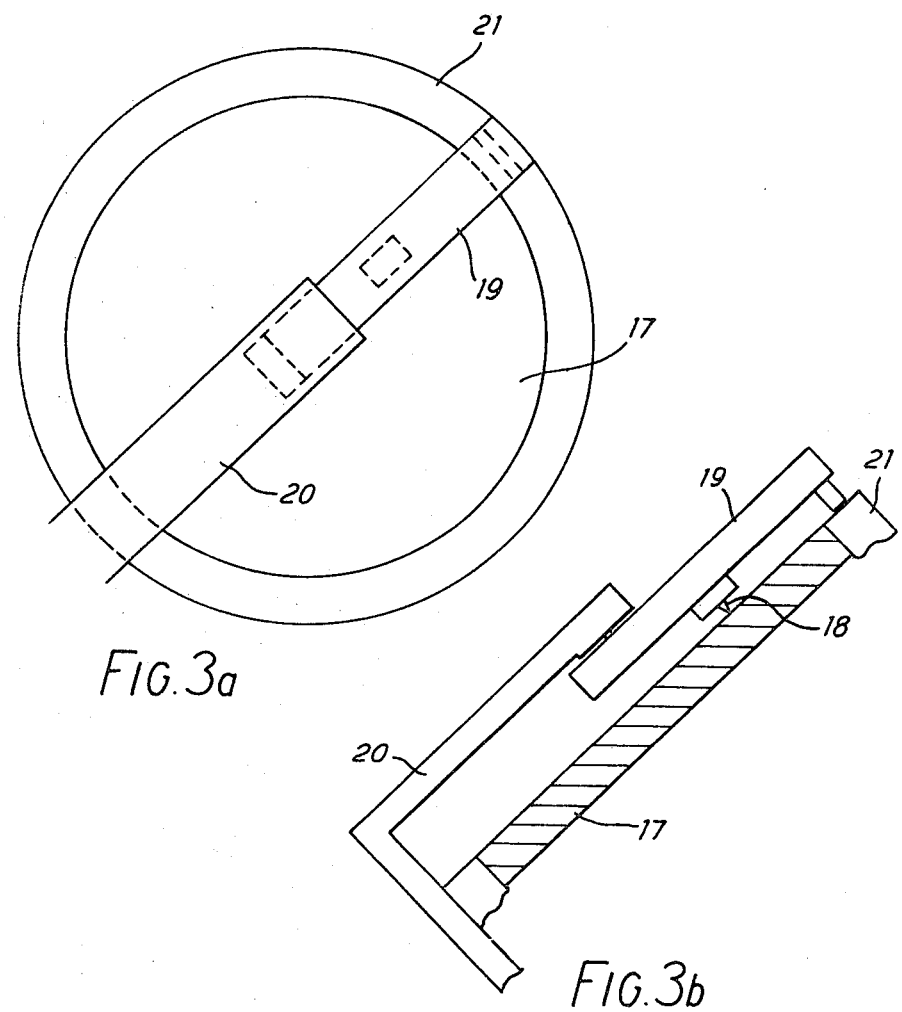

FIG. 3 shows another embodiment of the invention, wherein an anisotropic plate is used as a back-plate of a xenon X-ray detector chamber.

The anisotropic plate is constructed by binding thin insulated wires together with either Epoxy resin and an interleaved earth plane, or copper loaded Epoxy resin. A difficulty arises with such a system in reading off the information stored as charge on the individual wires. It is also essential to discharge all the conductors at the end of each picture for re-use of the plate on further exposures.

In this example, the back of the back-plate 17 is formed with a spiral groove very similar to that of a standard gramophone record groove. The spiral groove will, of course, continue to the centre. It will be appreciated that the individual wires are brought out to points along the groove and that, since the xenon chamber is stationary, the pick-up device, which contains an electrically conductive stylus 18, mounted on an arm 19 revolves around a fixed centre, with the stylus free to move radially along the arm. The arm rotates on a support member 20 which supports the arm at the centre of the back-plate. The outer end of the arm 19 runs on a support race 21.

It is necessary for the stylus to be as hard as possible and to have a very low coefficient of friction. A diamond stylus has the appropriate physical properties but is unfortunately a very poor electrical conductor. However, it is possible to dope dianond with antimony or other materials to improve its conductivity, and this expedient can reduce the resistivity to a useable level (less than about 10 M$\Omega$).

An alternative stylus material is Silicon Carbide, an electrical conductor the physical properties of which are almost as good as those of diamond.

It will be appreciated that, in order to increase the speed of the readout, it is possible to use a many-headed probe and multiple grooves. It may be preferable, in some circumstances, to scan in a linear, rather than a spiral, mode. It will also be appreciated that the charges collected by the stylus may be either discharged to earth or applied to a high impedance amplifier.

A variety of other method for interrogating the wires are possible, for instance:

The charge can be measured by a non-contacting method.

The non-contacting methods involve movement of the charge induced in a head plate brought near to the charged conductor. With small conductors, however, such measurement is normally very sensitive to the gap between the head and the wire.

The contacting probe can follow a rigidly described path based on X-Y co-ordinates to cover the plate, either continuously rubbing the surface or intermittently contacting the surface.

The head unit can "hunt" for the wires using a wire pattern recognition system. This is analogous to the optical tracking methods used in certain types of videodisc recording.

A number of techniques, such as flooding with a conducting evaporating liquid, introducing a source of alpha particles or dragging a wire 'brush' over the surface, are available for discharge the wires.

However, the grooved path reading head as described above, can automatically discharge as it reads, and more importantly, guarantee that future readings will not find part of the plate with remaining charge.

In one practical embodiment, the anisotropic plate was constructed by winding 30AWG (0.5 mm OD, 0.25 mm ID) Kynar insulated copper wire onto a coil mandrel, binding each layer winding with a film of "Isopon" epoxy resin. The resultant coil was baked at 80° C. and sectioned to produce a small area plate. In order to provide a well-defined earth plane, a sheet of commercial aluminium baking foil, 50 micron thick was introduced, during the winding process, between each layer spanning approximately one-sixth of the circumference. Great care was taken to ensure that one edge of the foil as in line from layer to layer. The coil was subsequently bake-cured and sectioned such that the aluminium foil was level with one surface but just below the other.

A photomicrograph of the finished plate is shown in FIG. 4. It will be realised that although the surface shown contains charge storage wires and the aluminium earth foils, these are below the surface on the other face and do not interfere with the reading process.

Initial tests were carried out by charging the storage wires to 10 V from a voltage source using the aluminium foil as the earth screen. The charge was found to decay with a time constant of about 200 $\mu$s. The actual wire capacitance was found by charging a wire to 20 V and then discharging and measuring the peak value. The peak value was 8.8 V corresponding to about 9 pF. The decay rate was recorded by periodically discharging wires until the measured values had reduced to 1/e of the original. The decay constant for Kynar wire was about 30 minutes.

There was no measurable cross-coupling between nearest neighbours, even within a layer where nearest neighbours were not screened.

It was found that with 3.2 R exposure (180 mm, 10 seconds at 28 mA and 120 kV$_p$) each wire recorded a voltage of 20–30 V.

In the manufacture of another plate, a coil was wound using 30 AWG "Tefzel" wire, again obtainable from BICC. Tefzel wire has a lower dielectric constant than Kynar (2.6 against 7.7) and a much higher volume resistivity. EPO-TEK430, a copper filled electrically conductive epoxy, made by Epoxy Technology Inc., was used as the binding material, and was found to possess a useful property in that if made fairly smooth prior to heat curing at about 85° C., the surface became a good insulator. This is almost certainly caused by oxidation of the copper particles. This property rendered it possible to make a highly conductive coil, polish the relevant areas and then bake leaving a highly resistive surface film.

As a result it was possible to make a plate in which each conductor was completely screened from its neighbour by bulk conduction through the epoxy but the surface of the plates was totally insulated between wires. This is shown in FIG. 5.

The coil exhibited substantial charge retention as after the application on a 20 V charge to the wires, no measurable deterioration was found over a period of 100 hours.

The capacitance was measured by recording the peak value obtained by discharging a 20 V charge and was found to be 3 pF.

As mentioned previously, various possibilities exist for interrogating the conductor array, varying from sweeping a "brush" of conductors over the surface to individually hunting for each conductor with an optically controlled readout head. Similarly, it is possible to measure the charge by contact and non-contact methods although contact methods are considered likely to be the more reliable. Discharging may be carried out either simultaneously with interrogation or by blanket methods such as α-particles or evaporating conducting liquids.

The preferred method of reading the wires at present is to discharge them on earth and measure either the stored voltage or the charge flow. This method is moderately insensitive to contact resistances and solves the discharge problem. As described above, this can be achieved by means of a spiral groove cut into the back of the plate with approximately the same pitch as an LP record. A needle runs in the groove, discharging the individual wires in a fixed sequence. The needle can be made of doped diamond, although silicon carbide can be used as an alternative. A to-and-fro scan may, in some circumstances, be preferred to the above-mentioned spiral.

What we claim is:

1. A detector for responding to a two-dimensional pattern of X-radiation emergent from an object under examination to generate discrete electrical signals indicative of the amounts of radiation received at each of many locations distributed over the pattern, said detector comprising a substantially flat chamber, containing a noble gas, with an X-ray previous input window disposed to receive said pattern of radiation and a back-plate for said chamber disposed opposite said window and containing a respective electrical contact member for each of said locations, the contact members being exposed to said gas and mutually insulated so as to create an array of capacitive probes each capable, when suitable operating potentials are applied to the chamber, of storing charge indicative of the amount of radiation at the appropriate location of said pattern, and said detector further including interrogation means for sequential interrogating said contact members to sense the charges stored thereby.

2. A detector according to claim 1 wherein said mutual insulation is provided by respective insulating jackets surrounding each contact member.

3. A detector according to claim 2 wherein said contact members and their respective jackets are immersed in a matrix of an electrically conductive solid.

4. A detector according to claim 1 wherein each contact member consists of an elongate conductor.

5. A detector according to claim 1 wherein said interrogation means includes a grooved path, defined in the surface of said back-plate at predetermined points along which are disposed connections to the various contact members and a pick-up device arranged to follow said grooved path and to traverse said connections to sequentially make connection with the various contact members.

6. A detector according to claim 5 wherein said path is a spiral.

7. A detection system including a detector according to claim 1 together with electrical circuits for processing said electrical signals and a display arrangement for displaying the processed signals.

* * * * *